(12) United States Patent (10) Patent No.: US 7,927,820 B2
Zhang et al. (45) Date of Patent: Apr. 19, 2011

(54) ASSAY SYSTEMS AND METHODS FOR DETECTING MOLECULES THAT INTERACT WITH MEMBRANE CHANNELS

(75) Inventors: Sui-Po Zhang, Bala Cynwyd, PA (US); Ellen E. Codd, Blue Bell, PA (US)

(73) Assignee: Janssen Pharmaceutica NV, Beerse (BE)

( * ) Notice: Subject to any disclaimer, the term of this patent is extended or adjusted under 35 U.S.C. 154(b) by 626 days.

(21) Appl. No.: 10/894,836

(22) Filed: Jul. 20, 2004

(65) Prior Publication Data

US 2006/0019317 A1 Jan. 26, 2006

(51) Int. Cl.
*G01N 33/53* (2006.01)
(52) U.S. Cl. ........................................ 435/7.2
(58) Field of Classification Search ........................ None
See application file for complete search history.

(56) References Cited

U.S. PATENT DOCUMENTS

| 4,568,649 A | 2/1986 | Bertoglio-Matte | |
|---|---|---|---|
| 2003/0166099 A1* | 9/2003 | Sabbadini et al. | 435/69.1 |
| 2007/0031814 A1* | 2/2007 | Roos et al. | 435/4 |

FOREIGN PATENT DOCUMENTS

| EP | 154734 A1 | 9/1985 |
|---|---|---|
| WO | WO 02/05860 A | 1/2002 |
| WO | WO 03/021271 A | 3/2003 |

OTHER PUBLICATIONS

International Search Report dated Jan. 5, 2006 for corresponding Appln. No. PCT/US2005/025428.
Cooper, Matthew A.: "Advances in Membrane Receptor Screening and Analysis" Journal of Molecular Recognition, vol. 17, No. 4, Jul. 2004, pp. 286-315, XP002359417.
Langmead, Christopher J. et al.: "Characterisation of the Binding of (3H)-SB-674042, a novel nonpeptide antagonist, to the human orexin-1 receptor" British Journal of Pharmacology, vol. 141, No. 2, Jan. 2004, pp. 286-315 XP002359417.
International Preliminary Report on Patentability for related application PCT/US2005/025428, issued Jan. 23, 2007.
International Search Report and Written Opinon for related application PCT/US2005/025428, mailed Jan. 5, 2006.
Cornell et al., "A biosensor that uses ion-channel switches," *Nature*, 1997: 387, pp. 580-583.
Denyer et al., "HTS approaches to voltage-gated ion channel drug discovery," *Drug Discovery Today*, 1998: 3, pp. 323-332.
Hillyard et al., "A New Conus Peptide Ligand for Mammalian Presynaptic $Ca^{2+}$ Channels," *Neuron*, 1992: 9, pp. 69-77.
Mintz et al., "P-Type Calcium Channels in Rat Central and Peripheral Neurons," *Neuron*, 1992: 9, pp. 85-95.
Neher, "Ion Channels for Communication between and within Cells," *Neuron*, 1992: 8, pp. 605-612.
Olivera et al., "Neuronal Calcium Channel Antagonists. Discrimination between Calcium Channel Subtypes using ω-Conotoxin from Conus magus Venom," *Biochemistry*, 1987: 26, pp. 2086-2090.
Randall et al., "Pharmacological Dissection of Multiple Types of $Ca^{2+}$ Channel Currents in Rat Cerebellar Granule Neurons," *J. Neurosci.*, 1995: 15, pp. 2995-3012.
Sasaki et al., "Combinatorial synthesis of ω-Conotoxin MVIIC analogues and their binding with N- and P/Q-type calcium channels," *FEBS Letters*, 2000: 466, pp. 125-129.
Wheeler et al., "Roles of N-Type and Q-Type $Ca^{2+}$ Channels in Supporting Hippocampal Synaptic Transmission," *Science*, 1994: 264, 107-111.
Whorlow et al., "Selectivity of ω-Conotoxin GVIA for N-Type Calcium Channels in Rat Isolated Small Mesenteric Arteries," *Clin. Exp. Pharmacol Physiol.*, 1996: 23(1), pp. 16-21.
Xu et al., "Ion-channel assay technologies: quo vadis?," *Drug Discovery Today*, 2001: 6, pp. 1278-1287.
Zhang et al., "Functional studies of bradykinin receptors in Chinese hampster ovary cells stably expressing the human $B_2$ bradykinin receptor," *Int. Immunopharmacol*, 2001: 1, pp. 955-965.
Zhang et al., "A Simple Statistical Parameter for Use in Evaluation and Validation of High Throughput Screening Assays," *J. Biomol. Screening*, 1999: 4, pp. 67-73.

* cited by examiner

*Primary Examiner* — Michael Pak

(57) ABSTRACT

The invention provides an assay system for detecting a molecule that interacts with a membrane channel, the assay system including cell membranes including one or more membrane channels; support bodies including scintillant and a coupling agent that associates with the cell membrane; a ligand that is selected to bind the membrane channel, the ligand including a scintillant-activating label. According to the invention, association of the support bodies with the cell membrane and binding of the ligand to the membrane channel results in emission from the scintillant of the support bodies, and, in the presence of a test molecule that interacts with the membrane channel, the emission from the scintillant of the support bodies changes. Methods of identifying a molecule that interacts with a cell membrane channel are also described.

11 Claims, 10 Drawing Sheets

ASSAY SYSTEMS AND METHODS FOR DETECTING MOLECULES THAT INTERACT WITH MEMBRANE CHANNELS

FIELD OF THE INVENTION

The invention relates to assay systems and methods for detecting molecules that interact with cell membrane channels. More particularly, the invention relates to scintillation proximity assay (SPA) systems and methods for detecting modulators of ion channels.

BACKGROUND OF THE INVENTION

Cell membranes include a number of channels through which molecules such as nutrients, waste products, ions, and small molecules pass. Ion channels are one example of membrane channels that are found in the membrane of all cells. Typical ion channels are composed of a trans-membrane protein or group of proteins that selectively allow the passage of ions through the membrane lipid bilayer. Named after the predominant ion passing through the channel, examples of ion channels include sodium ($Na^+$) channels, potassium ($K^+$) channels, chloride ($Cl^-$) channels, and calcium ($Ca^{2+}$) channels. An ion channel can be permanently open, such as is found in a potassium leak channel. An ion channel can also be voltage gated, and one example is the sodium channel. Alternatively, ion channels can be ligand gated. Ligand gated channels are ion channels whose permeability to ions is sensitive to the binding of a specific ligand, such as a neurotransmitter. Examples of neurotransmitters include, but are not limited to, acetylcholine, glutamate, glycine, or γ-aminobutyric acid. The category of membrane channels can also include membrane channels that are not ion-conducting, but rather permit passage of other molecules into and/or out of the cell.

The structures of ion channels differ among channel families. Each channel includes various protein subunits encoded by different genes that can be selectively expressed in certain cell types or during certain periods of development and growth of the organism.

Ion channels play a critical role in shaping the electrical activity of neuronal and muscle cells, as well as controlling the secretion of neurotransmitters and hormones. Because of their relevance to a variety of physiological processes in vertebrates, such as muscle contraction, insulin release from the pancreas, and neurotransmitter release in the nervous system, ion channel research has gained increasing importance to the pharmaceutical industry.

In particular, calcium channels are important targets for further research because they are ubiquitous ion channels that specifically mediate $Ca^{2+}$ passage into and out of cells. $Ca^{2+}$ entering the cell through voltage-gated $Ca^{2+}$ channels serves as the second messenger of electrical signaling: initiating events such as contraction, secretion, synaptic transmission, and gene expression. Calcium channels can be categorized as L-type (for long lasting), T-type (for transient), N-type (for neither L-type nor T-type, or for neuronal), P-type (for Purkinje cell), Q-type, and R-type (for resistant) based upon factors such as activation and inactivation kinetics, ion specificity, and sensitivity to drugs and toxins. Except for the T-type channel, which is a low voltage activated (LVA) channel, the L-, N-, P-, Q-, and R-types are high voltage activated (HVA). In other words, the HVA channels exhibit activation thresholds that are normally above −40 mV. Although L-type and T-type $Ca^{2+}$ currents are recorded in a wide range of cell types, N-, P-, Q-, and R-type currents are most prominent in neurons.

Design of an assay for identifying a new drug that has specific modulatory effects on an ion channel is hindered by the fact that the ion channel is made of multiple protein subunits, and the function of the ion channel can be evaluated only when the channel is within a membrane lipid bilayer. In particular, a compound identification assay for calcium channel modulation is complicated by such factors as: 1) native channel expression at low density; 2) difficulty to clamp by classical voltage-clamp methods (many ion channels that are candidates for study occupy cells that are difficult to clamp, and examples of these cells include dendrites, nerve terminals, and muscle cells due to their complex infoldings); and 3) the small current of ion channels tends to be masked by those of many other channels.

Existing technologies for identifying ion channel modulators are a compromise between throughput, physiological relevance, sensitivity and robustness. A widely accepted assay for studying ion channel function is the patch-clamp technique (Neher (1992), *Neuron*, 8:605-612). Although several companies are attempting to automate the patch-clamp process, the current complexity and reproducibility of the experimental setup currently renders it unsuitable for a high throughput screen (HTS) application. Optical recording using voltage sensitive dyes or radioisotopes has become popular for the study of voltage-gated ion channels, including calcium channels. Such methods are more readily automated and give much higher throughput for drug screening applications (currently, up to 100,000 compounds per day), and may provide a more sensitive measure of ion channel activity (Xu, et al. (2001), *Drug Discovery Today*, 6:1278-12887). However these assays frequently require pharmacologic intervention to activate the channels under investigation, leading to the possibility of generating false positive results (Denyer, et al. (1998), *Drug Discovery Today*, 3:323-332).

Another assay technique adaptable for HTS is the competitive binding assay. Typically, a vacuum filtration method is used to quantify the binding of a radio-labeled specific ligand to an ion channel. The ligand bound to the channel remains on the filter and the unbound free ligand is washed out with wash buffer. This procedure can be cumbersome because it takes a relatively long time and requires large volumes of wash buffer. Further, the separation procedures involve repeatedly washing with the wash buffer, thereby generating a large volume of radioactive liquid waste, which is not only expensive to dispose of, but also presents a potential health hazard to persons performing the experiment.

SUMMARY OF THE INVENTION

The present invention provides assay systems and methods of detecting molecules that interact with cell membrane channels. More particularly, the invention relates to scintillation proximity assay systems and methods for detecting modulators of ion channels. In preferred embodiments, the assay systems and methods of the invention can provide such advantages as high throughput, reduced cost in terms of resources and reagents required, and reduced waste. In preferred embodiments, the invention provides a homogeneous assay that can be performed in a single reaction mixture. Further, the invention preferably provides a system that reduces false positive results and/or background, thus generating reliable and reproducible assay results.

In one aspect, the invention provides an assay system for detecting a molecule that interacts with a cell membrane channel, the assay system comprising:

a. cell membranes that include one or more membrane channels;

b. support bodies comprising scintillant and a coupling agent that associates with the cell membrane;

c. a ligand that is selected to bind the membrane channel, the ligand comprising a scintillant-activating label, wherein association of the support bodies with the cell membrane and binding of the ligand to the membrane channel results in emission from the scintillant of the support bodies, and wherein, in the presence of a test molecule that interacts with the membrane channel, the emission from the scintillant of the support bodies changes.

In another aspect, the invention provides a method for identifying a molecule that interacts with a cell membrane channel, the method comprising steps of:

a. providing cell membrane that includes one or more membrane channels;

b. incubating the cell membrane with support bodies comprising scintillant and a coupling agent under conditions to allow the coupling agent to associate with the cell membrane;

c. incubating the cell membrane with a ligand comprising a scintillant-activating label under conditions to allow the ligand to bind the membrane channel;

d. incubating the cell membrane with a test molecule suspected to interact with the membrane channel;

e. measuring emissions from the scintillant of the support bodies when the test molecule is present and when the test molecule is absent; and f. comparing the emissions from the scintillant of the support bodies when the test molecule is present with emissions from the scintillant of the support bodies when the test molecule is absent.

BRIEF DESCRIPTION OF THE DRAWINGS

The accompanying drawings, which are incorporated in and constitute a part of this specification, illustrate several aspects of the invention and together with the description of the preferred embodiments, serve to explain the principles of the invention. A brief description of the drawings is as follows.

DETAILED DESCRIPTION OF THE INVENTION

Figure 1:
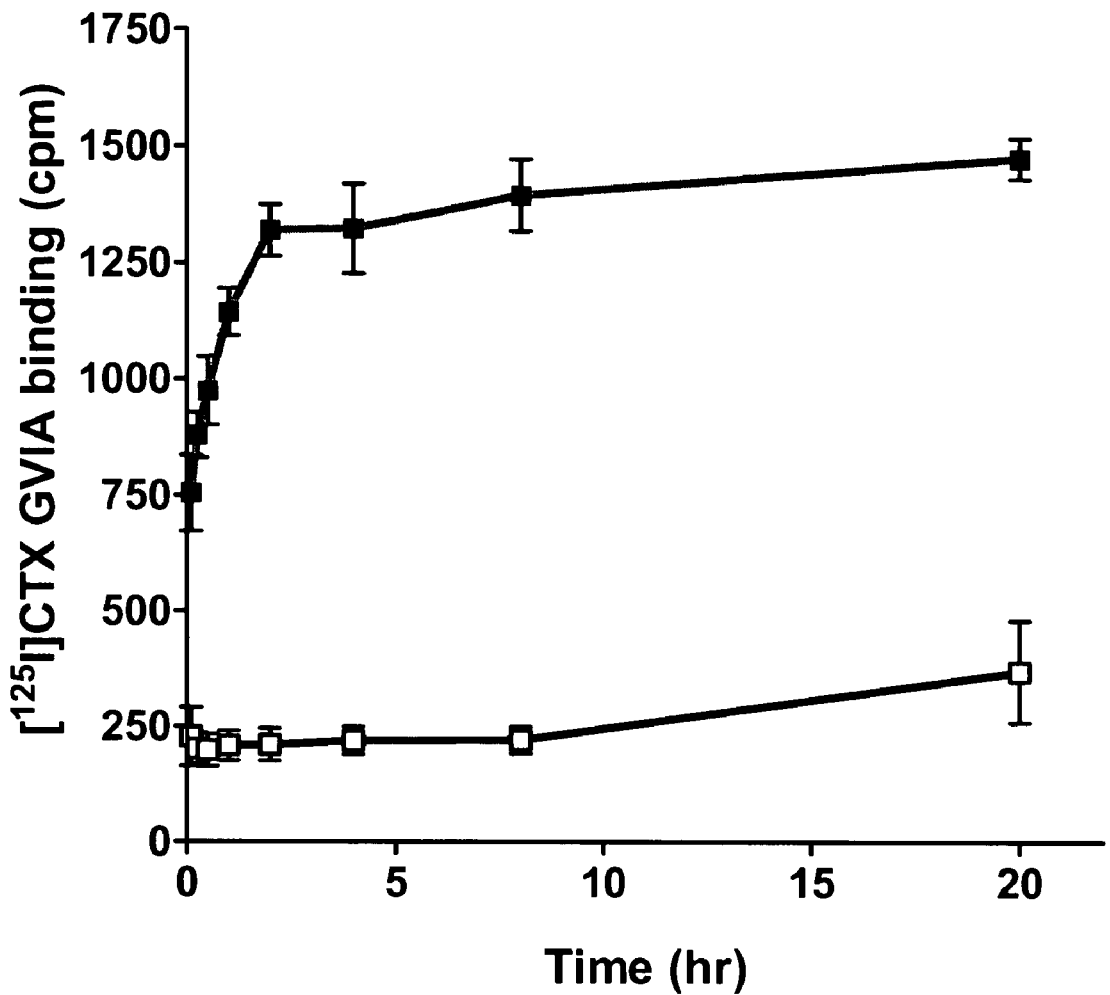
FIG. 1 is a graph illustrating the effect of incubation time in hours (X-axis) on the binding of [$^{125}$I]GVIA to ion channels in cell membranes isolated from rat brain, in counts per minute (cpm) (Y-axis), open square: non-specific binding (NSB); filled square: total binding.

All publications cited herein are hereby incorporated by reference. Unless defined otherwise, all technical and scientific terms used herein have the same meaning as commonly understood to one of ordinary skill in the art to which this invention pertains.

As used herein, the terms "comprising", "containing", "having" and "including" are used in their open, non-limiting sense.

As described herein, a "test molecule" means a molecule suspected to interact with a cell membrane channel, that is subjected to the assay systems and methods described herein. "Test molecule", "test compound", and "molecule suspected to interact with a membrane channel" will be used interchangeably herein.

The inventive assay systems and methods can be used to detect test molecules that interact with the membrane channel in any manner that affects the ability of the membrane channel to bind ligand, as will be appreciated upon review of the present teachings.

As used herein, ion channel "modulators" include molecules that interact with an ion channel in such a way as to affect the activity of the ion channel. Illustrative examples of modulators include molecules that decrease, block, prevent, delay activation, inactivate, desensitize or down regulate channel activity, or speed or enhance deactivation of the ion channel, such as, for example, channel inhibitors or blockers. Other illustrative examples of modulators include molecules that increase, open, activate, facilitate, enhance activation, sensitize or up regulate channel activity, or delay or slow inactivation of the channel, such as, for example, channel activators or openers.

The interaction of the ion channel "modulator" with the membrane channel of interest can be direct or indirect. Examples of direct interaction include binding of the molecule to the ligand binding site of the membrane channel. Indirect interaction includes interaction with any other site of the membrane channel in such a way as to affect the ability of the membrane channel to bind ligand. Such indirect interaction can include molecules that function as inhibitors or activators, for example.

As described herein, "support bodies" are physical particles comprising scintillant and a coupling agent. The support bodies can be provided in any suitable configuration to incorporate the scintillant and coupling agent such that the scintillant is available for receiving and emitting energy, and the coupling agent is available for associating with the cell membrane. Examples of the support bodies are the scintillation proximity assay beads (SPA beads), which are commercially available, for example, from Pharmacia Amersham. Other formats of the support body are contemplated, such as latex particles or other structures.

Optionally, the support bodies can further include a wavelength shifter such as 1,4-bis(5-phenyl-2-oxazolyl)benzene; 9,10-diphenylanthracene; 1,4-bis(2-emthylstyryl)-benzene, and the like. When present, the function of the wavelength shifter is to absorb the light emitted by the scintillant and re-emit longer wavelength light which is a better match to the photo-sensitive detectors used in scintillation counters.

The "scintillant" of the support bodies is an agent that is sensitive to radiation and which scintillates (for example, emits light energy) upon radiation exposure. The scintillant can be physically or chemically incorporated into the support bodies. Upon excitation by a radiolabeled reactant, the excited scintillant releases sufficient energy, which can be detected by a scintillation counter or other detection device, such as that utilizing a photomultiplier tube. Examples of the scintillant, include, but are not limited to cerium-loaded glass, materials based on rare earth methals such as yttrium silicate, lanthanide metal compounds, or a scintillant polymer, such as poly(vinyl toluene).

Examples of the scintillant also include a fluorescent material that gives off light energy upon excitation when it is brought in close proximity to a radiolabeled reactant. Fluorescent materials useful in the invention include any of the organic fluors well known in the scintillation counting art. Generally, suitable fluorescent materials can be selected, for example, from those described as "organic fluors" and "organic scintillators" in Organic Scintillation Detection, E. Schram and R. Lombaert, Elsevier Publishing Co., 1963. Examples of fluorescent materials include 2,5-diphenyloxazole (PPO); derivatives of the oxazoles and 1,3,4-oxadiazoles, such as 2-(4-t-butylphenyl)-5-(4-biphenylyl)-1-3,4-oxoadiazole and 2,5-diphenyloxazole; anthracene; 9,10-diphenylanthracene; p-terphenyl, p-quaterphenyl and their derivatives; 2-(4-biphenylyl)-5-(4-tert-butyl-phenyl)-1,3,4-oxadiazole (butyl PBD); PBD; 2-(1-Naphthyl)-5-phenyloxazole ($\alpha$-NPO); and the like. An example of a preferred scintillant that can be used with radioactive energy in the form of beta rays (such as that emitted from $^{14}C$, $^{35}S$, $^{33}P$, and $^{125}I$) is diphenyloxazole (PPO).

A number of materials can be used to provide a binder, matrix, or other support for the scintillant of the support bodies. Examples of suitable binder materials include polyacrylamide, acrylamide, agarose, polystyrene, polypropylene, polycarbonate, Sepharose, and the like. Beads, such as Sepharose 4B beads are available commercially (from Pharmacia Fine Chemicals, Uppsala, Sweden).

The method by which the scintillant is incorporated in the support body will depend upon such factors as, for example, the material used to form the support bodies, the scintillant, the desired loading density of scintillant in the support body, and the like. In one incorporation method, for example, the scintillant is adsorbed into a material that forms the support body. According to this particular embodiment, a solvent can be chosen in which the scintillant is soluble. Preferably, the scintillant is insoluble in water, and in these embodiments, the solvent would be chosen to be miscible in water. The material forming the support bodies is incubated in the solvent to dehydrate the material. Thereafter, the material can be incubated in solvent containing the scintillant, under conditions such that the scintillant is adsorbed into the material, thereby forming support bodies containing scintillant. Excess solvent can be discarded, and the scintillant is precipitated by adding water or a buffered saline solution, thereby locking the scintillant within the material of the support bodies. Suitable methods for integrating a scintillant into a support body, such as a bead, are described in U.S. Pat. No. 4,568,649 and EP 154,734.

The "coupling agent" of the support bodies is a molecule that associates with a cell membrane, for example, by binding to the cell membrane. Such association can be either non-specific or specific. For example, when the association is non-specific, the association relies upon such general characteristics of the cell membrane as its negative charge. In one example of a non-specific association, poly-L-lysine can bind to negatively charged cell membranes. For specific associations, the association can rely, for example, upon the presence of specific proteins located within or on the cell membrane surface. For example, wheatgerm agglutinin binds to N-acetyl-$\beta$-D-glucosamine containing oligosaccharides on membrane surfaces; streptavidin binds to biotinylated proteins, peptides and oligonucleotides; *Staphylococcus aureus* protein A can be used to bind antibody-antigen complexes; and antibodies can be chosen that bind specific sites on the cell membrane. Examples of coupling agents include poly-L-lysine, wheatgerm agglutinin, streptavidin, *S. aureus* protein A, antibodies, and the like.

Although reference is made herein to the ability of the coupling agent to bind the cell membrane, the invention does not require a binding interaction between the coupling agent and the cell membrane per se. To the contrary, any association between the coupling agent and the cell membrane that retains the support bodies at the surface of the cell membrane, such that the inventive assays can be performed, is suitable for use in the invention. In preferred embodiments, the binding affinity of the coupling agent for the cell membrane is in the range of from about 50 nM to about 1 pM.

The coupling agent can be associated with the support bodies using any suitable methods, depending upon such factors as the material used to form the support bodies, the scintillant, the particular coupling agent chosen, the desired loading density of coupling agent, and the like. In some embodiments, the coupling agent is incorporated into the support bodies using a linking agent such as, for example, cyanogen-bromide, carbodiimide, tannic acid, glutaraldehyde, or polyethylene glycol. The linking agent can be incorporated in the support bodies to covalently bind with the desired coupling agent. After incorporation of the coupling agent, a blocking agent (such as glycine, for example) can be used to block remaining active sites on the bead if desired, thereby reducing binding of the cell membrane directly to the support bodies, rather than the coupling agent.

The coupling agent can be incorporated in the material of the support bodies. Such incorporation can be physical (for example, entrapment) or chemical (for example, chemical binding). Alternatively, the coupling agent can be coated on the surface of the support body. The manner by which the coupling agent is incorporated in the support bodies is not critical, so long as the coupling agent is available for association with the cell membrane in accordance with the inventive assays.

In one illustrative embodiment, Sepharose 4B beads activated with cyanogen bromide, and a coupling agent in the form of *Staphylococcus aureus* protein A or an antibody to a specific cell membrane protein, can be incorporated in the support bodies by placing the support bodies in a solution containing the protein A or antibody and an appropriate buffer. Thereafter, the excess protein A (or antibody) can be washed away and the remaining active sites on the support bodies to which no protein A (or antibody) had attached are blocked with an appropriate blocking agent, such as glycine.

As used herein, a "scintillant-activating label" is a reactant that is capable of exciting a scintillant, and is associated with a ligand for a membrane channel. The scintillant-activating label is chosen depending upon the type of scintillant included in the support bodies. For example, the scintillant-activating label can comprise a radioactive isotope. Preferred radioactive isotopes are chosen to have only a limited range of radiation in water, so that for the most part, only the radioactive isotopes on the labeled ligand that binds to the membrane channel actually activates the scintillant of the support bodies bound thereon. Examples of suitable radioactive isotopes include $^{125}I$, $^{3}H$, $^{14}C$, $^{59}Fe$, $^{33}P$, $^{35}S$, $^{38}Sr$, and the like. In one preferred embodiment, where the scintillant chosen is PPO, isotopes that emit either beta rays or auger electrons from gamma ray emissions can be used.

The scintillant-activated label is incorporated into the ligand using suitable methods that do not substantially affect the ability (for example, specificity) of the ligand to bind the membrane channel. The method used for labeling will vary with the type of scintillant-activating label utilized. For example, labeling with radioactive isotope can be accomplished by replacing one of the atoms of the ligand with a corresponding radioactive isotope. According to this particular embodiment, for example, one or more hydrogen atoms can be replaced with tritium ($^{3}H$), one or more carbon atoms can be replaced with carbon-14 ($^{14}C$), or one or more strontium atoms can be replaced with strontium-38 ($^{38}Sr$). In another embodiment, an isotope can be added to the ligand, as opposed to replacing an atom within the ligand. Examples of such radioactive isotopes in common use include iodine-125 ($^{125}I$) and iron-59 ($^{59}Fe$). In situations in which biological organisms or parts of those organisms are capable of synthesizing proteins, labeling can be carried out by culturing the organism with an appropriate radiolabeled precursor, such as methionine-35 ($^{35}S$), to cause the organism to incorporate the isotope into its products.

The present invention is directed to systems and methods for detecting molecules that interact with a membrane channel. In preferred embodiments, the invention is directed to systems and methods for detecting molecules that interact with an ion channel. For illustrative purposes, the invention will be described with reference to ion channel modulators. However, it will be readily apparent upon review of the present disclosure that the inventive assay systems and methods can be used to identify many different types of molecules that interact with any type of membrane channel, utilizing the teachings herein.

The inventive assay systems and methods are used to detect molecules that interact with cell membrane channels. In preferred embodiments, the inventive assay systems and methods are used to identify modulators of ion channels.

The invention provides a method for identifying a molecule that interacts with a membrane channel, the method comprising steps of: (a) providing cell membrane that includes one or more membrane channels; (b) incubating the cell membrane with support bodies comprising scintillant and a coupling agent under conditions to allow the coupling agent to associate with the cell membrane; (c) incubating the cell membrane with a ligand comprising a scintillant-activating label under conditions to allow the ligand to bind the membrane channel; (d) incubating the cell membrane with a test molecule suspected to interact with the membrane channel; (e) measuring emissions from the scintillant of the support bodies when the test molecule is present and when the test molecule is absent; and (f) comparing the emissions from the scintillant of the support bodies when the test molecule is present with emissions from the scintillant of the support bodies when the test molecule is absent. The information collected in step (f) is used to assess molecule interaction with the membrane channel of interest. In preferred embodiments, the invention is used to detect a modulator for a membrane channel.

Generally speaking, in one aspect, the invention utilizes two moieties, support bodies and ligand which interact, preferably at the cell membrane, to output information indicative of the interaction of a test compound with a membrane channel. The support bodies associate with the cell membrane utilizing the coupling agent incorporated into the support bodies and comprises the scintillant. The ligand specifically binds the membrane channel of the cell membrane and comprises a scintillant-activating label. The assay is designed to utilize the spatial separation between the scintillant (of support bodies) and scintillant-activating label (of ligand) to determine whether a modulator interacts with the membrane channel of interest.

In one illustrative embodiment, the scintillant-activating label of the ligand is a radioisotope, for example, $^{125}I$. $^{125}I$-labeled ligand binds the membrane channel, and support bodies associate with the cell membrane. When the $^{125}I$ emits radiation of wavelength $\lambda_1$, this radiation is received by the support bodies, and the scintillant of the support bodies then emits fluorescent radiation of wavelength $\lambda_2$ that can be detected. Since the average range of $^{125}I$ rays in water is relatively short, any aqueous medium in which the reaction is suspended can serve as an effective absorber of emissions. As a result, unbound $^{125}I$ will not contribute to detectable signal output; rather, emissions from the unbound $^{125}I$ will be absorbed by the aqueous medium. Detection of the output signal is readily carried out with a standard liquid scintillation counting system energy gated for $^{125}I$ testing.

In general, when the energy emitted by the scintillant-activating label has a limited range of traveling in water, unbound ligands are typically located too far away from the scintillant to excite the scintillant. As a result, there is no need to wash the membrane complexes or remove unbound ligand containing scintillant-activating label prior to measuring assay signal. Thus, the present assay systems and methods provide a homogeneous system that avoids additional washing and/or separation steps prior to reading the results of the assay.

Preferably, the support body is provided with dimensions suitable for the proximity assay described herein. For example, typical diameters of the support bodies in preferred embodiments are optimized to allow the scintillant contained in the support bodies to be in close enough physical relationship to the labeled ligand, when both the support body and the labeled ligand are associated with the cell membrane and membrane channel, respectively, such that energy emitted from the scintillant-activating label reaches the scintillant of the support body and causes the scintillant to emit energy. Typically, the diameter of the support body is less than the activation range of the scintillant. For example, typical diameter of poly(vinyl toluene) (PVT) beads is approximately 5 µm, while typical diameter of yttrium silicate (YSi) beads is approximately 2.5 µm.

In preferred embodiments, support bodies are provided at a concentration in the range of about 0.75-5 mg/ml of the assay reaction solution. Preferably, support bodies are incubated with the cell membrane at temperature in the range of room temperature (20-25° C.) to about 37° C., with pH conditions in the range of about 4 to about 8.

The invention provides competitive binding assays to detect molecule(s) that interact with a membrane channel of interest. As discussed above, the labeled ligand binds the membrane channel of interest. When both the molecule(s) and labeled ligand are present in the assay mixture, and the test molecule(s) interact with the membrane channel of interest, therefore, the two moieties will compete for binding of the membrane channel. Generally speaking, if the molecule interacts (for example, binds or otherwise affects the binding of the ligand to) the membrane channel, therefore, labeled ligand will remain in solution. Because of the short length emissions of the scintillant-activating label in an aqueous solution, emissions from the label in solution will terminate in the solution and will not give rise to any output signal to be detected.

In other words, the proximity of the ligand to the support bodies is measured according to the assay; when the ligand and support bodies are within an activation range, the ligand induces the scintillant of the support bodies to emit detectable energy. The activation range is the distance from the support bodies that is equal to the range of emissions from the scintillant-activating label in the reaction solution. The assay is based on a measurement of the occurrence of two events to form a complex: (1) binding of the labeled ligand to the membrane channel and (2) association of support bodies to the cell membrane, forming a ligand/membrane channel-support body/cell membrane complex. This measurement can be utilized to detect a molecule or molecules that, by interaction, competitively displaces the labeled ligand to a location outside the activation range. If the molecule(s) interact (for example, bind) with the membrane channel, displaced labeled ligand will be unable to bind membrane channel and thus will remain in solution and outside the activation range. Emissions from the labeled ligand will thus be absorbed by the aqueous reaction solution. Output signal from the scintillant of the support bodies is correspondingly reduced. If, on the other hand, the molecule(s) do not interact with the membrane channel, more labeled ligand binds membrane channel and is thus located within the activation range. Output signal from the scintillant of the support bodies will be correspondingly increased. Preferably, the extent to which the labeled ligand/membrane channel-support body/cell membrane complex forms can be inferred (or determined by comparison with standard curves) by the intensity of the $\lambda_2$ band radiation arriving at the detector.

In embodiments of the invention, the reaction medium is aqueous, the pH is in the range of about 3 to about 9, and the temperature of the medium is in the range of about 25° C. to about 37° C. during the assay.

According to the invention, the cell membrane is incubated with support bodies comprising scintillant and coupling agent under conditions to allow the coupling agent to associate with the cell membrane. The cell membrane contains one or more membrane channels. According to the invention, cell membranes can comprise whole cells, portions of cell membranes, and/or membrane vesicles. Cell membranes can be obtained from any suitable type of animal cell, including human, rat, and the like. Whole cells can be isolated and treated using methods known in the art for cell preparation, including mechanical or enzymic disruption of the whole tissue, or by cell culture. In some embodiments, it can be preferable to utilize whole cells as the source of cell membrane, for example, when the cell membrane preparation procedure can destroy or inactivate cell receptors.

In some preferred embodiments, membranes can be broken under controlled conditions, yielding portions of cell membranes and/or membrane vesicles. Cell membrane portions and/or vesicles can, in some embodiments, provide an easier format for the inventive assays and methods, since cell lysis and/or shear is not as much of a concern during the assay. Cell membranes can be derived from tissues and/or cultured cells. Such methods of breaking cell membranes and stabilizing them are known in the art. Methods of treating tissues to obtain cell membranes are also known in the art.

The membrane channels contained within the cell membrane can be native membrane channels that are expressed endogenously by a cell, or membrane channels that are recombinantly expressed from exogenous DNA that is introduced into a cell. Isolation of cell membranes is known in the art, and methods of constructing a recombinant host cell for a membrane channel (for example, ion channels) are also known in the art.

In another embodiment, membrane channels can be incorporated into artificial membranes (see Cornell, B A, et al. (1997), *Nature* 387,580-583). For example, such artificial membranes can include an electrode to which is tethered a lipid membrane containing ion channels and forming ion reservoirs.

The inventive assay systems and methods of this invention can be utilized in connection with a variety of membrane channels. Such membrane channels include ion channels, ligand-gated channels, and the like. While the present description describes the invention with respect to one particular class of channels, e.g., ion channels, it will be readily apparent that the teaching herein can be applied to a variety of membrane channels that are present in a cell membrane.

In preferred embodiments of the invention, 0.5 µg or more of the cell membrane is present in each 200 µl assay reaction solution. Preferably, cell membrane is present in an amount of about 0.5 to about 20 µg per 200 µl assay reaction solution. In another aspect, cell membrane is preferably present in a concentration of about 2.5 mg/ml or greater, preferably in the range of from about 2.5 to about 100 mg/ml of the assay reaction solution.

The amount of membrane channels included in the cell membranes will vary depending upon the source of cell membranes. For example, in naturally occurring cell membranes, the concentration of channels within the cell membrane preparation may vary by species (for example, human versus rat membrane). The source of membranes can be considered when determining the amount of cell membranes to be included in the assay, to achieve a desired membrane channel concentration.

According to the invention, the cell membranes are incubated with a ligand comprising a scintillant-activating label under conditions to allow the ligand to bind the membrane channels.

For purposes of discussion herein, a ligand that includes a scintillant-activating label is also referred to as a "labeled ligand." The ligand is chosen to bind the membrane channels of interest, and in some particular embodiments, the ligand can even block conductivity through the membrane channels. The ligand of the invention is substantially biologically and chemically identical to an unlabeled ligand, with the exception of the scintillant-activating label that is capable of exciting a scintillant when they are in proximity. In the context of the previous sentence, "substantially biologically and chemically identical" means that the ligand containing scintillant-activating label is configured to interact with the membrane channels of interest in a way substantially similar to that of an unlabeled ligand (that is, a ligand lacking the scintillant-activating label). In other words, incorporation of the scintillant-activating label does not significantly interfere with the structure or function of the ligand, and in particular, does not significantly interfere with the interaction of the ligand with the membrane channel of interest.

Examples of suitable ligands according to the invention include antibodies, peptides, or small molecules. Examples of suitable antibodies include any antibodies that specifically bind a membrane channel of interest. According to the invention, antibodies can be monoclonal or polyclonal, and can comprise full length proteins or fragments (for example, Fc or F(ab)').

Many peptides have been identified that bind membrane channels, and any of these can be utilized in accordance with the present invention. For example, for the calcium channels, ligand peptides include, but are not limited to, spider and cone snail peptide toxins (See for example Mintz et al, (1992) *Neuron* 9:85-95; Randall et al., (1995) *J. Neurosci.* 15:2995-3012). For the sodium channel, well-investigated specific blockers include, but are not limited to, the peptide toxins in scorpion venoms and in nematocysts of coelenterate tentacles, the alkaloidal toxins secreted by tropical frogs, and other lipid-soluble, insecticidal substances obtained from the leaves of many types of plants (see Hille, *Ionic channels of excitable membranes*, $2^{nd}$ ed., Sinauer Associates, Inc., Sunderland, Mass.). For the potassium channel, examples of suitable ligand peptides include, but are not limited to, toxins, such as those listed in the table below. Examples of suitable ligands and their corresponding ion channels are summarized in Table I below. Where the ligand is naturally occurring, the source of ligand is also indicated.

TABLE I

Exemplary ligands for ion channel assays.

| Ion channel | Peptide | Source |
|---|---|---|
| $Ca^{2+}$ channel | | |
| N-type | ω-conotoxin MVIIA | *Conus magnus* |
| | ω-conotoxin GVIA | *Conus geographus* |
| | ω-conotoxin CVID (AM336) | *Conus* sp. |
| | ω-conotoxin CVIA | *Conus* sp. |
| | ω-conotoxin CVIB | *Conus* sp. |
| | ω-conotoxin CVIC | *Conus* sp. |
| | ω-conotoxin SVIB | *Conus striatus* |
| | ω-conotoxin TVIA | *Conus* sp. |
| | ω-conotoxin CNVIIA | *Conus* sp. |
| | ω-conotoxin PtIIA | *Conus* sp. |
| | ω-AgoIIIA | *Agelenopsis* sp. |
| | ω-conotoxin MVIIC | *Conus magnus* |
| P/Q-type | ω-agatoxin-IVA | *Agelenopsis aperta* |
| Q-type | ω-conotoxin MVIIC | *Conus magnus* |
| T-type | Mibefradil | |
| L-type | 1,4-dihydropyridines | |
| | Phenylalkylamines | |
| | Benzothiazepines | |
| | BAYK8644 | |
| $Na^+$ channel | Tetrodotoxin | *Tetradon stellatus* and other fish of *Tetraodontiformes* order |
| | Local anesthetics (e.g., lidocaine) | |
| | μ-conotoxin GIIIB peptide toxin | *Conus geographus* |
| | Anticonvulsants (e.g., lamotrigine, phenytoin) | |
| | Antiarrhythmics (e.g., quinidine, mexiletine) | |
| | Batrachotoxin | *Phyllobates aurotaenia* |
| | Aconitine | *Aconitum* sp. |
| | Veratridine | *Veratum* sp. |
| | Scorpion venom | *Leiurus quinquestriatus* |
| | ATXII | *Anthopleura xanthogrammica* |
| | Phyrethorids (insecticides) | *Chrysanthemum* sp. |
| | Brevetoxins | *Ptychodiscus brevis* |
| $K^+$ channel | | |
| Kv1.1, 1.2, 1.6 | α-dendrotoxin peptide | *Dendroaspis angusticeps* |
| Kv1.3 | Charybdotoxin peptide | *Leiurus quinquestriatus hebreaus* |
| Kv1.3 | Margatoxin | *Centruoides margaritatus* |
| Kv1, Kv3, Kv4.2 | 4-aminopyridine | |
| Kv1.1, 1.6, 2.1, Kv3 | Tetraethylammonium ions | |
| $Ca^{2+}$-activated $K^+$ (BK/hslo) | Paxilline alkaloid toxin | *Penicillium paxilli* |
| | Iberiotoxin peptide | *Buthus tamulus* |
| | NS1608 | |

In particular, GVIA, first isolated from the venom of *Conus geographus*, is a 27-amino acid peptide that is a potent and selective blocker of N-type calcium channels (Whorlow et al., *Clin Exp Pharmacol Physiol*. 1996, 23(1):16-21). MVIIA (also known as zincontide or SNX-111), was first isolated from the venom of *Conus magnus* and is a 25-amino acid peptide that is a potent N-type calcium channel blocker (Olivera et al., (1987) *Biochemistry* 26:2086-2090). MVIIC, isolated from the venom of *Conus magnus*, is a 26-residue peptide and is a weak inhibitor of N-type calcium channels and a potent inhibitor of P/Q-type calcium channels (Hillyard et al., (1992) *Neuron* 9:69-77; Wheeler et al., (1994) *Science* 264: 107-111; Sasaki et al., (2000) *Febs Letters* 466:125-129). ω-Agatoxin IVA is isolated from the spider *Agelenopsis aperta*, is a 48-amino acid peptide and has been shown to bind to the P/Q-type calcium channels (Mintz et al, (1992) *Neuron* 9:85-95).

In yet further embodiments, the ligand comprises a small molecule that binds the membrane channel of interest. Examples of suitable small molecules include antagonist drugs (calcium channels); as well as tetraethylammonium ions, and antiarrhythmic drugs such as nifedipine and quinidine (potassium channels); organic molecules such as disulfonic stilbenes, the arylaminobenzoates and sulfonylurea compounds (chloride channels). Additionally, the crystalline alkaloid capsaicin can be used.

For ligand-gated channels, endogenous specific ligands such as acetylchloine, glutamate, glycine, or γ-aminobutyric acid, can be used in accordance with some embodiments of the invention.

The affinity of the ligand for the membrane channel of interest can affect the sensitivity of the assay. For example, a high affinity ligand may not allow the detection of weakly binding molecules; on the other hand, a low affinity ligand could lead to increased detection of non-specific binding. Thus, in preferred embodiments, the affinity of the ligand is selected to be within a desired range such that the $EC_{50}$ values obtained from the assays have a reasonable correlation to those obtained from such traditional methods as patch-clamping. For example, the affinity of the ligand for the membrane channel is preferably selected to be in the range of about 1 pM to about 50 nM, more preferably in the range of about 5 pM to about 50 pM.

In preferred embodiments, the ligand is present in an amount in the range of about 10 pM to about 50 pM, preferably about 12 pM to about 20 pM, most preferably about 15 pM.

Many ligands are readily available in radiolabeled form from various commercial sources.

In preferred embodiments, choice of reagents and reaction conditions are controlled to reduce non-specific binding of the labeled ligand. According to these embodiments, such undesired non-specific binding includes binding of the labeled ligand to any sites other than the membrane channel of interest. For example, such non-specific binding can involve membrane lipids and other proteins located in the membrane. In other instances, such non-specific binding can involve binding of the labeled ligand directly to support bodies, or to the assay container itself. Non-specific binding is non-saturable but is approximately linearly related to the total concentration of the ligand present in the sample. When it occurs, non-specific binding increases background counts and consequently decreases the specific signal measured in the assay.

Generally, the observed total ligand binding is the sum of the saturable (hyperbolic) specific binding of the ligand to a corresponding receptor (in the present case, the membrane channel) and the non-saturable (linear) binding of the ligand to miscellaneous sites (that is, sites other than the membrane channel of interest). This relationship can be expressed as follows: (Total binding)=(specific binding to membrane channel)+(nonspecific binding to other sites). The specific binding component is typically obtained indirectly by carrying out the binding studies in the presence of excess non-labeled ligand. The non-labeled ligand competes with labeled ligand for binding of the membrane channel. Due to the excess non-labeled ligand, the specific binding sites (the membrane channel binding sites) would not be available to the experimental ligand and hence its binding is confined to non-specific sites.

Non-specific binding can be reduced by selecting appropriate components for the assay based upon the components' compatibilities with each other and/or the assay format. In one preferred embodiment, for example, when ω-conotoxins are used as the ligand, the preferred support bodies are PVT beads coated with wheatgerm agglutinin. In preferred embodiments, non-specific binding is maintained at a level that provides optimal signal to noise ratio.

In addition, assay conditions such as the pH of the buffer, the presence of specific ions or organic molecules, and/or the incubation time, can be optimized to reduce non-specific binding. In further embodiments, additives can be included in the buffer system to reduce non-specific binding. Typical NSB reducing agents include bovine serum albumin (BSA), polyethyleneimine (PEI), salts and detergents. Furthermore, assay containers such as microtiter plates made from materials such as those with non-binding surfaces (NBS) can reduce non-specific binding of the ligand to the assay container.

According to the invention, the cell membrane is incubated with a test molecule suspected to interact with the membrane channel. In accordance with the invention, the support bodies associate with the cell membrane, and the ligand containing scintillant-activating label binds the membrane channel of interest. When this occurs, the scintillant contained in the support bodies is stimulated to emit energy. Emissions from the scintillant when the test molecule is present are then compared with emissions from the scintillant when the test molecule is absent. A change (for example, decrease) in emissions when the test molecule is present is indicative of interaction of the test molecule with the membrane channel of interest.

As will now be described in more detail, the particular order of the incubation steps of the assay can be modified as desired. For example, in some embodiments, the cell membrane, support bodies comprising scintillant and a coupling agent, ligand comprising a scintillant-activating label, and the test molecule suspected to interact with the membrane channel are added to the assay as separate, sequential additions. In other words, in this embodiment, steps (a) through (d) are performed as separate, sequential steps in the assay. Preferably, this embodiment does not require any separation or washing steps, and all reagents are added directly to the assay medium sequentially. These particular embodiments can provide advantages, such as a simplified assay format and procedure. Further, there is no need for a pre-incubation period prior to the assay, and thus reagents can be reconstituted or thawed on the day of the assay. In some embodiments, this particular format allows easy optimization of the ratio of membrane to support bodies, as a matrix experiment can be set with varying membrane and varying support body concentrations. Preferably, a slight excess of support body is utilized to ensure a complete capture of all of the cell membrane present in the assay. One of skill in the art can utilize known methods for determining the optimum concentration of support bodies to be used in the assays described herein. The particular sequence of additions is not considered critical to the invention.

In some embodiments, the cell membrane is pre-incubated with the support bodies, under conditions to allow the cell membrane and support bodies to form membrane-support body complexes prior to the addition of additional reagents of the assay. According to this embodiment, the cell membrane and support bodies are pre-incubated before adding the cell membrane or labeled ligand to the assay. Generally, as one representative way to accomplish this, the cell membrane and support bodies are gently agitated for a pre-incubation period (typically one to four hours) at a desired temperature (typically 2-8° C.). This particular embodiment can provide advantages, such as reducing the number of additions made to the assay, since the support bodies and membranes are added as a single reagent. In some embodiments, this embodiment can provide uniformity in assay conditions, since the same preparation is used for each reaction solution of the assay.

Alternatively, in some embodiments, the cell membrane is pre-incubated with the ligand labeled with a scintillant-activating label, under conditions to allow the cell membrane and ligand to form membrane-ligand complexes prior to the addition of additional reagents of the assay. According to this embodiment, the amount of support bodies added is sufficient to associate with all of the cell membranes in the assay reaction mixture. The additional volume introduced will cause the equilibrium of bound to free ligand to shift, so the reaction should be given sufficient time to re-equilibrate before measurements are taken. In some embodiments, the incubation times for this format of the assay can be shorter than when reagents are added in a sequential manner.

Preferably, in all of the embodiments described herein for performing the inventive methods, the ratio of cell membranes to support body is optimized such that all, or substantially all of, the cell membranes present in the assay are associated with (for example, bound to) support bodies. Labeled ligand that is bound to uncoupled membrane (membrane that is not associated with support bodies) will not contribute to the assay signal, because the labeled ligand is located too far from the scintillant of the support bodies to affect emissions from the scintillant. In the embodiments where addition of reagents is sequential, or the ligand is pre-incubated with the cell membrane, it is preferred to include a slight excess of support bodies to ensure capture of all cell membrane by the support bodies.

In a typical performance of the invention, the signal as the ligand binds to the membrane channel and the support body associates with the cell membrane will continue to increase until the assay equilibrates. Alternatively, measurements can be taken at particular time points, t, during the assay. Generated output is detected by any suitable detector that utilizes a photomultiplier tube. Any suitable scintillation counter commercially available can be used as the detector.

As described herein, the invention provides a method for identifying a molecule that interacts with a membrane channel. Thus, when the molecule suspected to interact with the membrane channel is present in the assay sample, the molecule will compete with the ligand containing a scintillant-activating label for binding of the membrane channel of interest. As a result, when the molecule binds the membrane channel, it displaces labeled ligand, thereby reducing the light energy emitted from the scintillant, as the ligand containing a scintillant-activating label is removed from proximity to the scintillant. If the molecule is more competitive, a measurable change in the assay output will be observed.

Preferred embodiments of the invention can thus provide a number of advantages, such as a system allowing high-throughput screening of molecules suspected to interact with a membrane channel of interest. Further, according to preferred embodiments of the invention, the time required to complete the assay is limited only by the ligand-membrane channel reaction rate of the system under investigation. According to the invention, only the ligands containing scintillant-activating label that are bound to the cell membranes are in close enough proximity to the scintillant of the support bodies to allow the radiation energy emitted by the labeled ligand to bombard the scintillant. As a result, there is no need to wash the support bodies or otherwise attempt to remove the unbound labeled ligand from the reaction mixture; instead, the level of emitted energy can be measured with all of the components in the assay mixture present.

The following Examples illustrate various aspects of the invention.

EXAMPLES

Reagents and Methods
Binding Buffer: 50 mM hepes-Tris, pH 7.4, and 0.05% bovine serum albumin (BSA)
PVT-WGA Beads: Poly(vinyl toluene)—Wheatgerm Agglutinin SPA beads (commercially available from Amersham, Piscataway, N.J., Cat. No. RPNQ0001).
Ysi-WGA Beads: Yttrium Silicate—Wheatgerm Agglutinin SPA beads (commercially available from Amersham, Piscataway, N.J., Cat. No. RPNQ0011).
Ysi-PL Beads: Yttrium Silicate—Wheatgerm Agglutinin SPA beads (commercially available from Amersham, Piscataway, N.J., Cat. No. RPNQ0010).
[$^{125}$I] GVIA: PerkinElmer Life Sciences, Boston, Mass., Cat. No: NEX239
[$^{125}$I] MVIIC: PerkinElmer Life Sciences, Boston, Mass., Cat. No: NEX323
[$^{125}$I] MVIIA: PerkinElmer Life Sciences, Boston, Mass., Cat. No: NEX316
Unless otherwise indicated, SPA beads were used in a concentration of 5 mg/ml for the Examples below.
Preparation of Cell Membranes:
Cell membranes were prepared from human neuroblastoma cells (IMR32), differentiated by bromodeoxyuridine, or adult male Sprague-Dawley rat brain tissue according to procedures described in Zhang et al., (2001) *Int. Immunopharmacol* 1:955-965. Briefly, cells or tissue were homogenized in ice-cold 25 mM Tris (pH 7.2), 2 mM EDTA and 320 mM sucrose. After homogenization, the suspension was first centrifuged at 100×g for 10 minutes. The resulting supernatant was collected and then centrifuged at 40,000×g for 20 minutes. The membrane pellet was collected, resuspended in Binding Buffer and stored at −70° C. The protein concentration in the membrane preparation was determined using the Bradford Reagent (Bio-Rad) with bovine serum albumin (BSA) as a standard. Cell membrane was present in an amount of 2-5 mg/ml. Typically, calcium channels are present in an amount of about 200 fmol/mg rat brain membrane protein.

Example 1

Specific Binding of Ligand to Calcium Channel

This example illustrates a method for measuring specific binding of a ligand to a calcium channel contained within cell membrane isolated from rat brain tissue.

Assays were performed at room temperature (20° C.-25° C.) in a 96-well microtiter plate. To each well, 2.5 µg of cell membrane (as measured by protein concentration) isolated from rat brain tissue as indicated above, 1 mg PVT-WGA Beads, and Binding Buffer in an amount to bring the total reaction solution to a volume of 200 µl were incubated at room temperature for one (1) hour, at pH 7.4. This pre-incubation step allowed formation of cell membrane/bead complexes.

Following incubation, 15 pM of one of the following labeled ligands was added to each well: [$^{125}$I] GVIA, or [$^{125}$I] MVIIC. The resulting reaction mixture was incubated at room temperature, pH 7.4, for 60 minutes.

For non-specific binding studies, 100 nM unlabeled GVIA conotoxin was added to each well prior to adding [$^{125}$I] GVIA, and the reaction mixture was incubated for one (1) hour at room temperature, pH 7.4, to allow equilibration to be attained. The unlabeled GVIA conotoxin was present in excess, such that all available calcium channel specific binding sites were bound by the unlabeled ligand prior to addition of labeled GVIA.

Light energy emitted from the microtiter plate was measured using a Packard Top Count™ scintillation counter. Increase in light energy corresponded to formation of membrane-bead complexes.

Results for binding of GVIA are illustrated in FIG. 1. Incubation with [$^{125}$I]GVIA was performed for various time periods (zero to 20 hours), as noted above and represented on the X-axis of FIG. 1. [$^{125}$I]GVIA binding is represented on the Y-axis, in cpm. Total binding of ligand is shown at curve A (filled square), while non-specific binding is shown at curve B (open square). Specific binding of GVIA to calcium channel is obtained by determining the difference between total binding (curve A) and non-specific binding (curve B).

Figure 7:
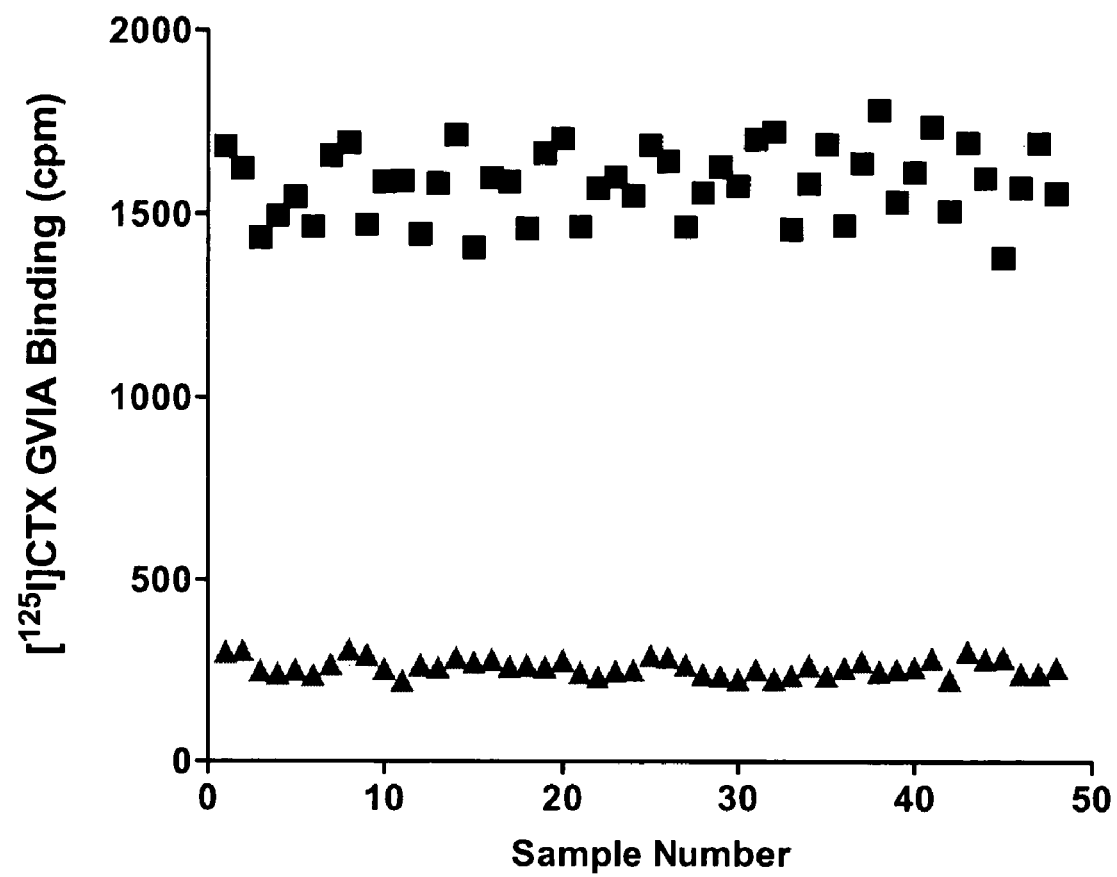
FIG. 7 is a graph illustrating the total [$^{125}$I]GVIA binding to membrane channels in cell membranes (represented in squares) and nonspecific binding to cell membranes (represented in triangles) isolated from rat brain, for calculation of the Z factor. Sample number is represented on the X-axis, and [$^{125}$I]GVIA binding, in cpm, is represented on the Y-axis.

To determine well-to-well variance, 48 total binding samples and 48 non-specific binding samples were tested in a 96-well plate. The assay procedure was followed as outlined above in this Example 1. Results are illustrated in FIG. 7, which illustrates [$^{125}$I]GVIA binding cpm (Y-axis) for total binding and NSB samples. Sample numbers are represented on the X-axis. Total binding is represented with squares in the Figure, and nonspecific binding is represented with triangles. As shown, when total binding measured 1641.3 counts per minute (cpm), non-specific binding (NSB) measured 264 cpm. Thus, the specific binding of GVIA (Total binding—NSB) was determined to be 1377 cpm. The calculated ratio of total binding to non-specific binding was approximately 6. The Z-factor (Zhang et al., 1999, *J. Biomol. Screening*, 4:67-73) was approximately 0.75, suggesting that the reproducibility of this assay is sufficient for the conduct of high throughput screening.

Example 2

Effects on Binding of Labeled Ligand to Cell Membrane

The effect of concentration of support bodies, cell membrane concentration, and ligand concentration on binding of labeled ligand to cell membrane was determined.
Support Body Concentration The effects of varying the concentration of support bodies in the presence of set concentrations of labeled ligand and cell membrane were examined. Wells having varying concentrations of SPA beads (0.75 to 5 mg/ml) were prepared in a microtiter plate. To each well, 2.5 µg cell membranes isolated from rat brain tissue and Binding Buffer were combined in an amount to bring the total reaction solution volume to 200 µl. The reaction mixture was incubated for one (1) hour at room temperature, pH 7.4.

As a control, 100 nM unlabeled GVIA was added to each well, and the reaction mixture was incubated for one (1) hour at room temperature, pH 7.4. The unlabeled GVIA was present in excess, such that all available calcium channel specific binding sites were bound by the unlabeled ligand.

15 pM [$^{125}$I] GVIA was then added to each well, and the reaction mixture was incubated for one (1) hour at room temperature, pH 7.4, to allow equilibration to be attained.

Figure 2:
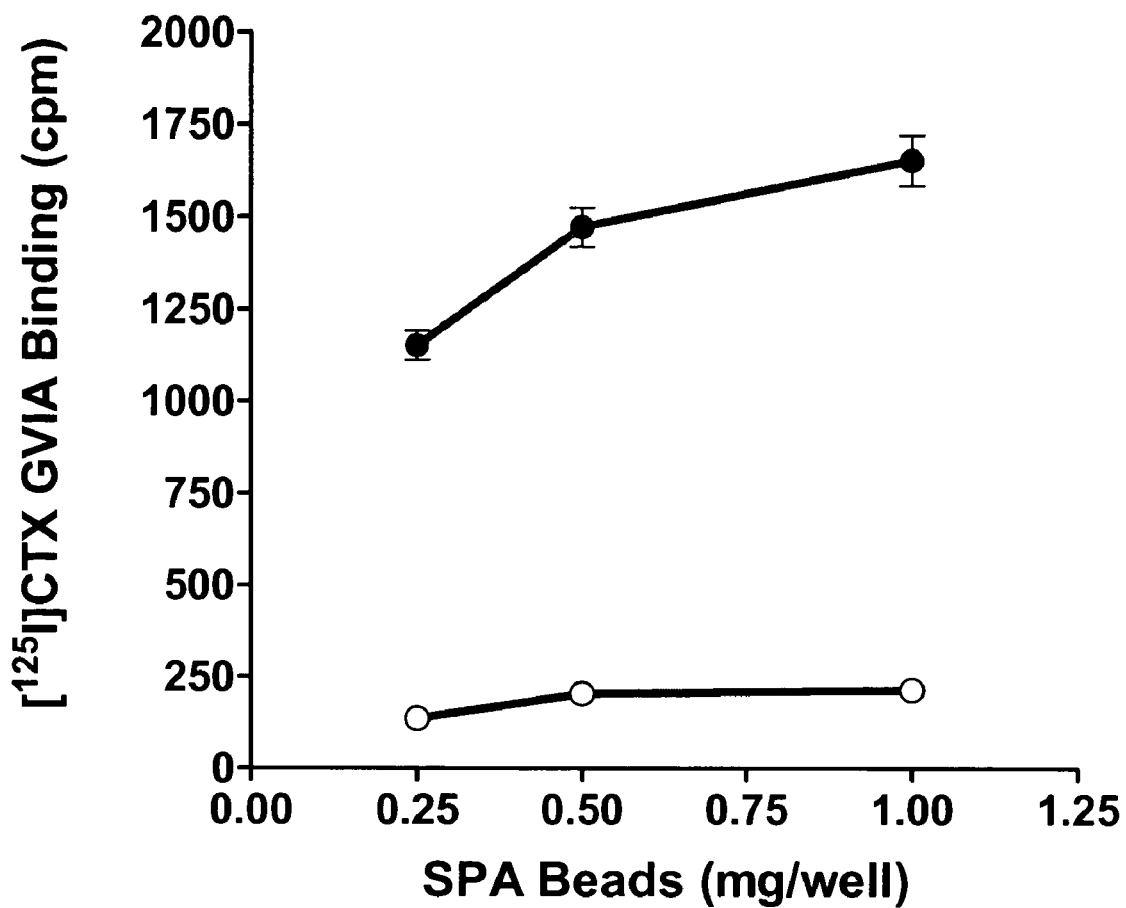
FIG. 2 is a graph illustrating the effect of bead concentration in mg/well (X-axis) on the binding of [$^{125}$I]GVIA to ion channels in cell membranes isolated from rat brain, in cpm (Y-axis), open circle: non-specific binding (NSB); filled circle: total binding.

Light energy emitted from the microtiter plate was measured using a Packard Top Count™ scintillation counter. Results are shown in FIG. 2. Concentration of SPA beads (mg/well) is illustrated on the X-axis, and [$^{125}$I]GVIA binding in cpm is illustrated on the Y-axis. Increase in light energy corresponds to formation of bead-membrane complexes. As illustrated in FIG. 2, binding of [$^{125}$I] GVIA to cell membranes was dependent upon the concentration of PVT-WGA Beads present. Total binding of labeled-GVIA is represented at curve A (dark circles), while non-specific binding of labeled-GVIA is represented at curve B (open circles).
Cell Membrane Concentration The effects of varying cell membrane concentrations in the presence of set concentrations of labeled ligand and support bodies were examined. Varying concentrations (3.125 to 25 mg/ml) of cell membranes obtained from rat brain tissue were placed in wells of a microtiter plate. To each well, 1 mg PVT-WGA beads and Binding Buffer in an amount to bring the total reaction solution volume to 200 µl were added. The reaction mixture was incubated for one (1) hour at room temperature, pH 7.4.

Following incubation, 100 nM unlabeled GVIA was added to each well, and the reaction mixture was incubated for one (1) hour at room temperature, pH 7.4. The unlabeled GVIA was present in excess, such that all available calcium channel specific binding sites were bound by the unlabeled ligand.

15 pM [$^{125}$ I] GVIA was then added to each well, and the reaction mixture was incubated for one (1) hour at room temperature, pH 7.4, to allow equilibration to be attained.

Figure 3:
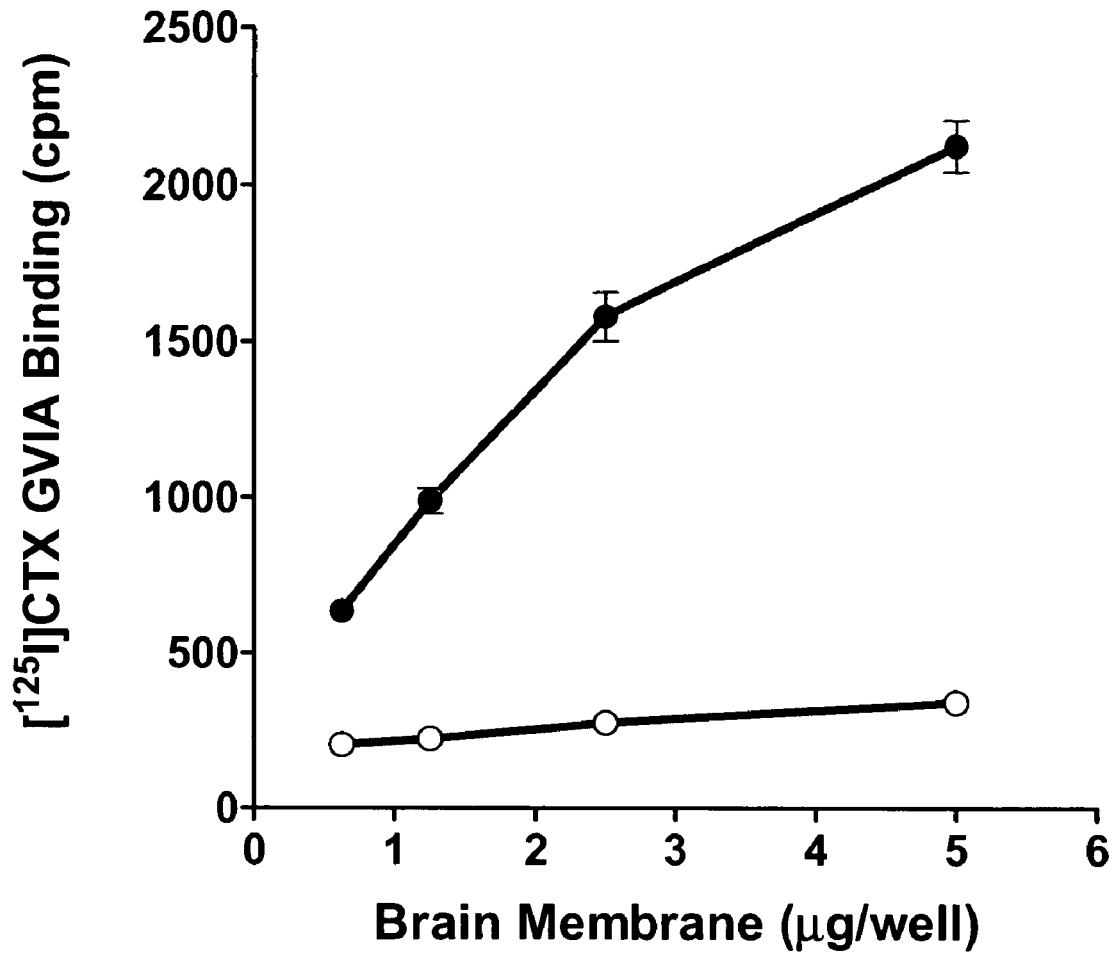
FIG. 3 is a graph illustrating the effect of cell membrane concentration in μg/well (X-axis) on the binding of [$^{125}$I]GVIA to ion channels in cell membranes isolated from rat brain, in cpm (Y-axis), open circle: non-specific binding (NSB); filled circle: total binding.

Light energy emitted from the microtiter plate was measured using a Packard Top Count™ scintillation counter. Results are shown in FIG. 3. Concentration of brain membrane is illustrated on the X-axis (µg/well), and [$^{125}$I]GVIA binding is illustrated on the Y-axis (cpm). Increase in light energy corresponds to formation of bead-membrane complexes. As illustrated in FIG. 3, the formation of bead-membrane complex was dependent upon the concentration of the cell membrane present in the assay mixture. Total binding of labeled-GVIA is shown at curve A (dark circles), while non-specific binding of labeled-GVIA is shown at curve B (open circles).
Ligand Concentration The effects of varying labeled ligand concentrations in the presence of set concentrations of support bodies and cell membranes were examined. 1 mg PVT-WGA Beads, 2.5 µg cell membranes isolated from rat brain, and Binding Buffer in an amount to bring the total reaction solution volume to 200 µl were placed in each well of a 96-well microtiter plate. The reaction mixture was incubated for one (1) hour at room temperature, pH 7.4.

Following incubation, 100 nM unlabeled GVIA was added to each well, and the reaction mixture was incubated for one (1) hour at room temperature, pH 7.4. The unlabeled GVIA was present in excess, such that all available calcium channel specific binding sites were bound by the unlabeled ligand.

Varying concentrations of [$^{125}$I] GVIA (1 to 100 pM) were then added to each well, and the reaction mixture was incubated for one (1) hour at room temperature, pH 7.4, to allow equilibration to be attained.

Figure 4:
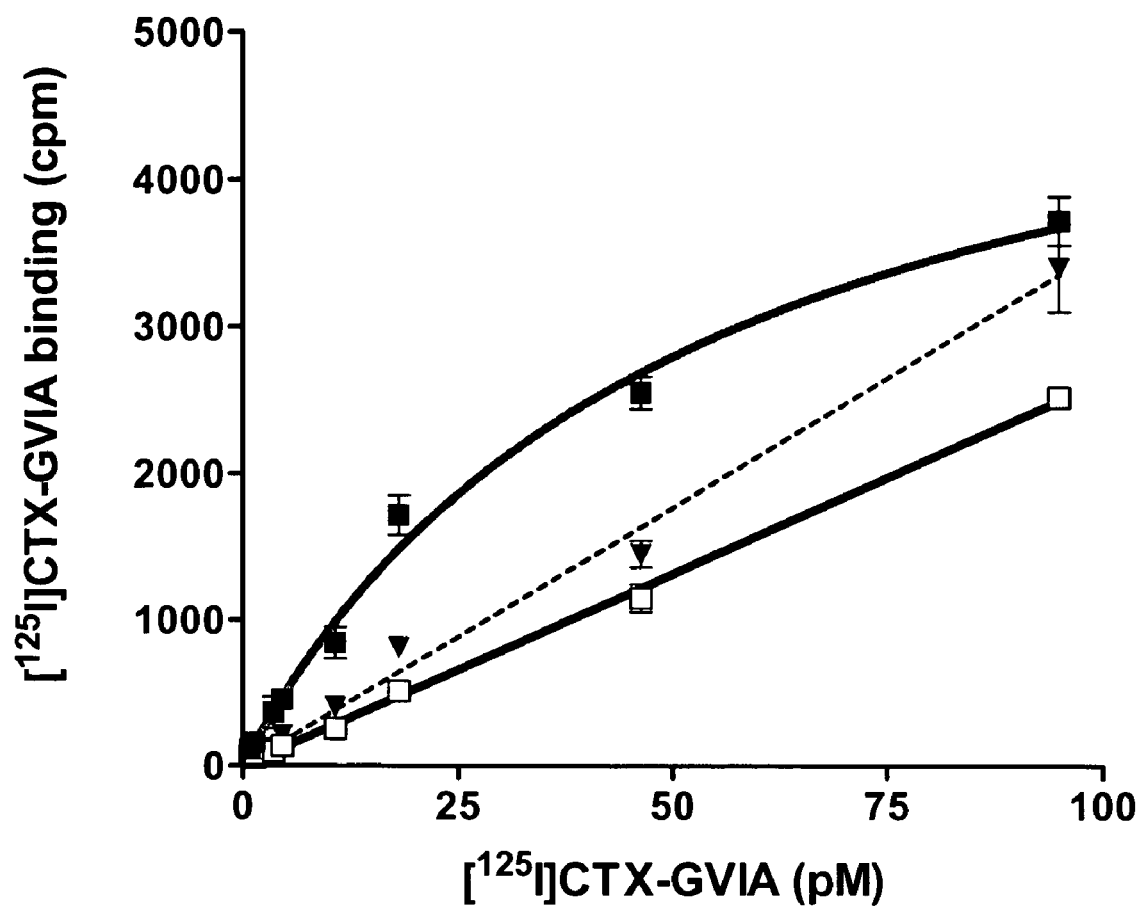
FIG. 4 is a graph illustrating the effect of ligand concentration in picomolar, pM (X-axis) on the binding of [$^{125}$I]GVIA to ion channels in cell membranes isolated from rat brain, in cpm (Y-axis), open square: non-specific binding (NSB); dark square: total binding; dark triangle, background (BKG).

Light energy emitted from the microtiter plate was measured using a Packard Top Count™ scintillation counter. Results are shown in FIG. 4. Concentration of [$^{125}$I]GVIA is illustrated on the X-axis in pM, and [$^{125}$I]GVIA binding is illustrated on the Y-axis in cpm. Increase in light energy corresponds to formation of bead-membrane complexes. FIG. 4 illustrates the effect of [$^{125}$I]GVIA concentration on binding of the labeled ligand to the cell membranes. Background (curve B, triangles) was determined in the absence of cell membranes. Total binding of ligand is illustrated at curve A (dark squares), while non-specific binding is illustrated at curve C (open squares).

Figure 5:
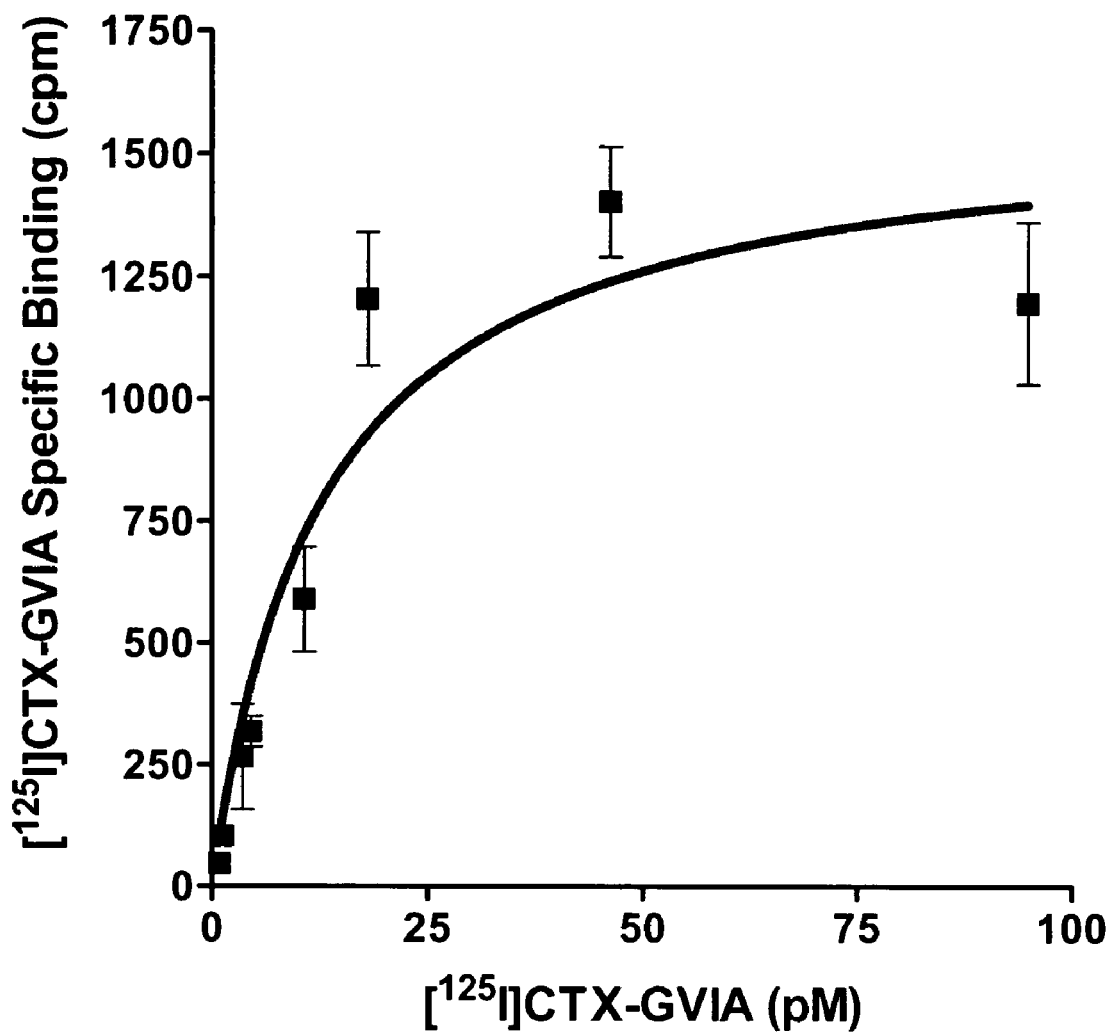
FIG. 5 is a graph illustrating the effect of ligand concentration in pM (X-axis) on the binding of [$^{125}$I]GVIA to ion channels in cell membranes isolated from rat brain, in cpm (Y-axis). Data in this figure is a replot of data in FIG. 4.

FIG. 5 illustrates that the binding of [$^{125}$I]GVIA to the cell membranes is saturable at higher concentrations of ligand. Concentration of [$^{125}$I]GVIA in pM is illustrated on the X-axis, and [$^{125}$I]GVIA binding in cpm is illustrated on the Y-axis. The data illustrated in FIG. 5 is a replot of the data represented in FIG. 4. The computer-drawn curve represents the best fit to the data. Half-maximal binding ($EC_{50}$) was reached at a concentration of approximately 12 pM, while maximal binding ($B_{max}$) was reached at a concentration of approximately 25 pM. Analysis of the saturation data for [$^{125}$I]GVIA showed that the binding was best fit using a one-site model, with a dissociation constant ($K_d$) value of 13 pM and $B_{max}$ value of 225 fmol/mg protein.

Example 3

Competitive Binding of Calcium Channel

The ability of other calcium channel ligands to compete with [$^{125}$I]GVIA for binding to cell membranes isolated from rat brain was studied as follows.

In each well of a 96-well microtiter plate, the following was added: 1 mg WGA-PVT Beads, 2.5 µg rat cell membranes isolated from rat brain tissue, and Binding Buffer in an amount to bring the total reaction solution volume to 200 µl. The reaction mixture was incubated for one (1) hour at room temperature, pH 7.4.

Following incubation, 15 pM [$^{125}$I]GVIA was added to each well, and the reaction mixture was incubated for one (1) hour at room temperature, pH 7.4.

The ability of various ligands to compete for binding to the cell membranes was studied by adding one the following ligands to the reaction mixtures prepared above: GVIA, MVIIA, MVIIC, and ω-Agatoxin. Each ligand was added in concentrations of 0.1 pM to 0.1 µM. The reaction mixtures were incubated for one (1) hour at room temperature, pH 7.4, to allow equilibration to be attained.

Figure 6:
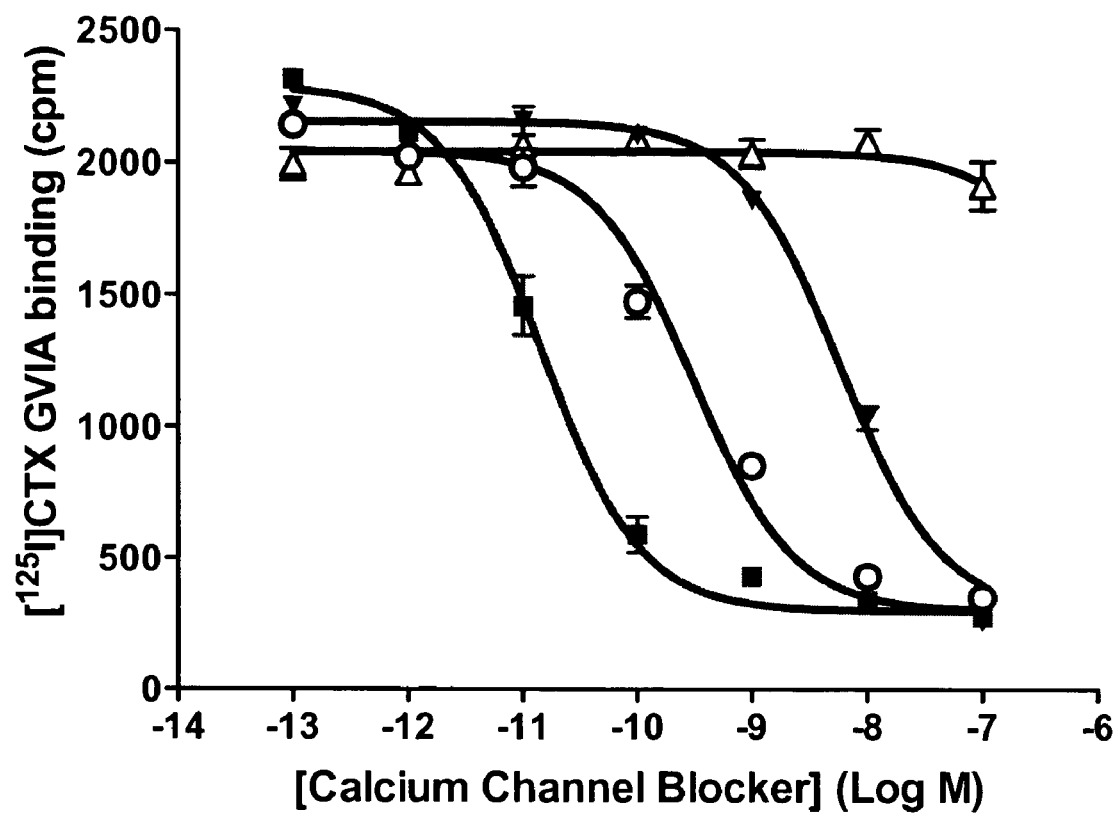
FIG. 6 is a graph illustrating the effect of the presence of competitive ligands on the binding of [$^{125}$I]GVIA to ion channels in cell membranes isolated from the rat brain. The log of the concentration of competitive ligand is represented on the X-axis, and the binding of [$^{125}$I]GVIA, in cpm, is represented on the Y-axis, square: CTX-GVIA; circle: CTX-MVIIA; dark triangle: CTX-MVIIC; open triangles, ω-Agatoxin.

Light energy emitted from the microtiter plate was measured using a Packard Top Count™ scintillation counter. Results are illustrated in FIG. 6, which illustrates binding curves for each of the ligands studied. Inhibition curves were best fit by single-site binding models. The concentration of ligand is represented on the X-axis (log M), and [$^{125}$I]GVIA binding is represented on the Y-axis (cpm). Binding of GVIA is shown at curve A (squares), MVIIA is shown at curve B (circles), MVIIC is shown at curve C (dark triangles), and ω-Agatoxin is shown at curve D (open triangles). Displacement of [$^{125}$I]GVIA binding to the cell membranes was observed in the following order: GVIA>MVIIA>MVIIC>>ω-Agatoxin. In other words, GVIA exhibited the highest relative binding affinity, while ω-Agatoxin exhibited the lowest relative binding affinity of the ligands assayed. GVIA, MVIIA and MVIIC binding data were best fit by one-site models. The results indicate that [$^{125}$I]GVIA specifically bound to N-type calcium channels in cell membranes isolated from rat brain.

The affinity constant ($K_i$) for each of the ligands was calculated, and results are shown below in Table 2. The data demonstrate that the assay method provides a valid system to study competitive binding interactions with calcium channels.

TABLE 2

| | Affinity Constants for Specific Ligands | | | |
|---|---|---|---|---|
| | GVIA | MVIIA | MVIIC | ω-Agatoxin |
| $K_i$ | $8.29 \times 10^{-12}$ | $1.37 \times 10^{-10}$ | $3.97 \times 10^{-9}$ | $>1 \times 10^{-7}$ |

Example 4

Binding of Ligand to Cell Membranes

Binding of two different ligands to cell membranes isolated from rat brain was studied as follows.

Assays were performed at room temperature in a microtiter plate. In a first set of reactions designed to detect [$^{125}$I]MVIIA binding, 2.5 µg of cell membranes isolated from rat brain tissue as indicated above, 1 mg PVT-WGA Beads, and Binding Buffer in an amount to bring the total reaction solution volume to 200 µg were added to each well and incubated for one (1) hour at room temperature, pH 7.4. In a second set of reactions designed to detect [$^{125}$I]MVIIC binding, 5 µg of cell membrane isolated from rat brain tissue as indicated above, 1 mg PVT-WGA Beads, and Binding Buffer to bring the total reaction solution volume to 200 µl were added to each well and incubated for one (1) hour at room temperature, pH 7.4. This pre-incubation step allowed formation of cell membrane/bead complexes.

After the above incubation, 15 pM [$^{125}$I]MVIIA were added to the first set of reactions, and 15 pM [$^{125}$I]MVIIC were added to the second set of reactions. Reaction mixtures were incubated for one (1) hour at room temperature, pH 7.4, to allow equilibration to be attained.

Non-specific binding was tested in the presence of 100 nM unlabelled MVIIA (first set of reactions) or MVIIC (second set of reactions), as appropriate to the reaction mixture, using the procedure of Example 1.

Figure 8:
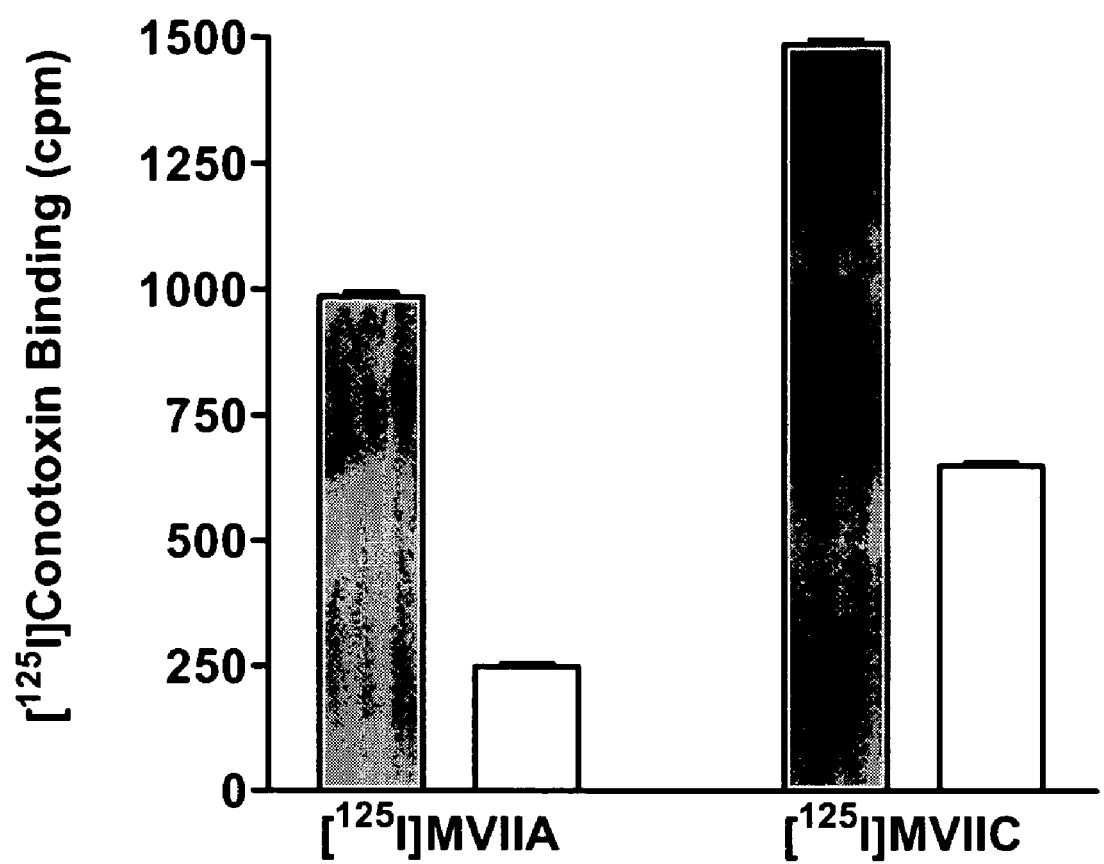
FIG. 8 is a graph illustrating the binding of [$^{125}$I]MVIIA or [$^{125}$I]MVIIC to ion channels in cell membranes isolated from rat brain using one embodiment of the invention. Total binding is represented as a gray bar, and nonspecific binding is represented as a white bar.

Light energy emitted from the microtiter plate was measured using a Packard Top Count™ scintillation counter. Results are shown in FIG. 8. Total binding for each ligand is shown at bar A, while nonspecific binding for each ligand is shown at bar B. [$^{125}$I] conotoxin binding (MVIIA for first set of reactions, MVIIC for second set of reactions) is shown in cpm on the Y-axis.

Example 5

Binding of Ligands to IMR32 Cells

Binding of labeled ligands to IMR32 cells was studied as follows. Assays were performed at room temperature in a microtiter plate. To each well, 10 µg of cell membrane isolated from IMR32 cells as indicated above, 1 mg PVT-WGA Beads, and Binding Buffer in an amount to bring the total reaction solution volume to 200 µl were added to each well and incubated at room temperature for one (1) hour, pH 7.4. This pre-incubation step allowed formation of cell membrane/bead complexes.

After incubation, 15 pM [$^{125}$I]GVIA) first set of reactions) or [$^{125}$I]MVIIA (second set of reactions) were added to the reaction mixtures. Reaction mixtures were incubated for one (1) hour at room temperature, pH 7.4, to allow equilibration.

Non-specific binding was tested in the presence of 100 nM unlabelled GVIA (first set of reactions) or MVIIA (second set of reactions), as appropriate to the reaction mixture, using the procedure of Example 1.

Figure 9:
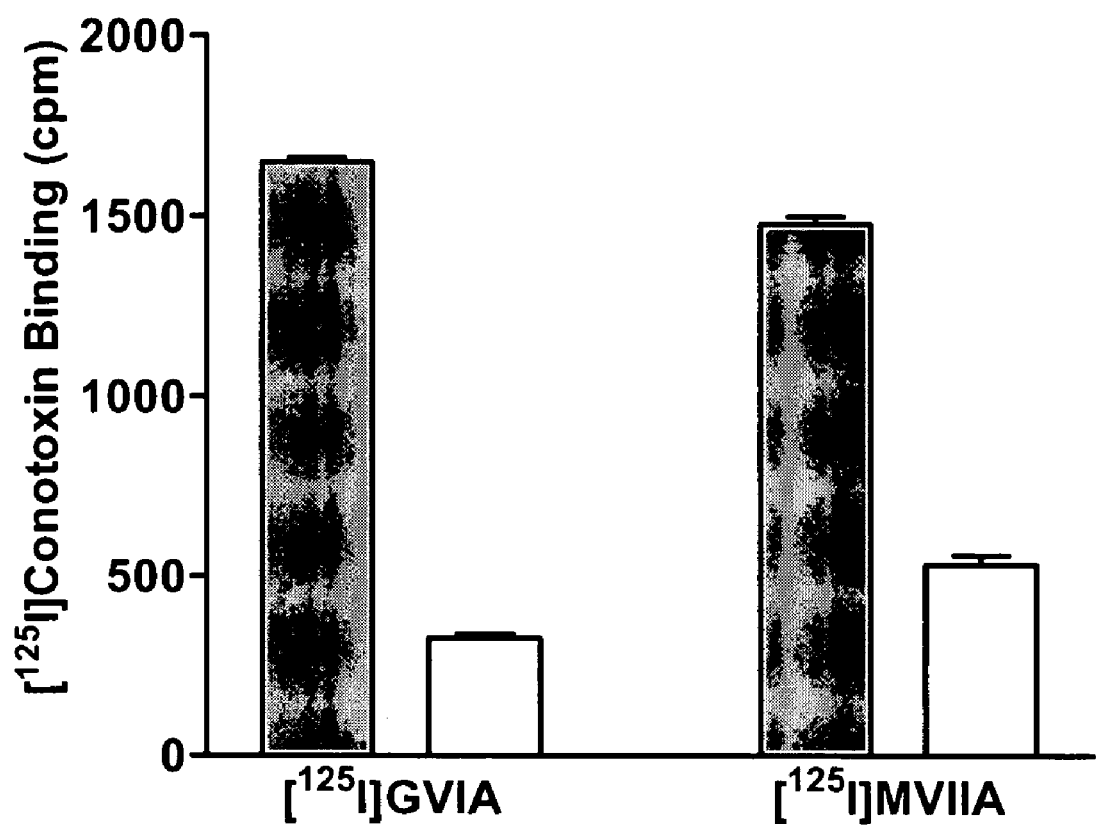
FIG. 9 is a graph illustrating the binding of [$^{125}$I]GVIA or [$^{125}$I]MVIIA to ion channels in cell membranes isolated from IMR32 cells using one embodiment of the invention. Total binding is represented as a gray bar, and nonspecific binding is represented as a white bar.

Light energy emitted from the microtiter plate was measured using a Packard Top Count™ scintillation counter. Results are shown in FIG. 9. Total binding for each ligand is shown at bar A, while nonspecific binding for each ligand is shown at bar B. [$^{125}$I] conotoxin binding (GVIA for first set of reactions, MVIIA for second set of reactions) is shown in cpm on the Y-axis.

Example 6

Binding of Beads Containing Varied Coupling Agent

The ability of support bodies containing varied coupling agents to associate with cell membranes and to function in a ligand-binding assay was studied as follows.

Assays were performed at room temperature in a microtiter plate. To each well, 2.5 μg of cell membrane isolated from rat brain tissue, 1 mg Ysi-WGA Beads or Ysi-PL Beads, and Binding Buffer in an amount to bring the total reaction solution volume to 200 μl, were added to each well and incubated at room temperature for one (1) hour, pH 7.4. This pre-incubation step allowed formation of cell membrane/bead complexes.

After incubation, 15 pM [$^{125}$I]MVIIA were added to the reaction mixtures. Reaction mixtures were incubated for one (1) hour at room temperature, pH 7.4, to allow equilibration.

Non-specific binding was tested in the presence of 100 nM unlabelled MVIIA, using the procedure of Example 1.

Figure 10:
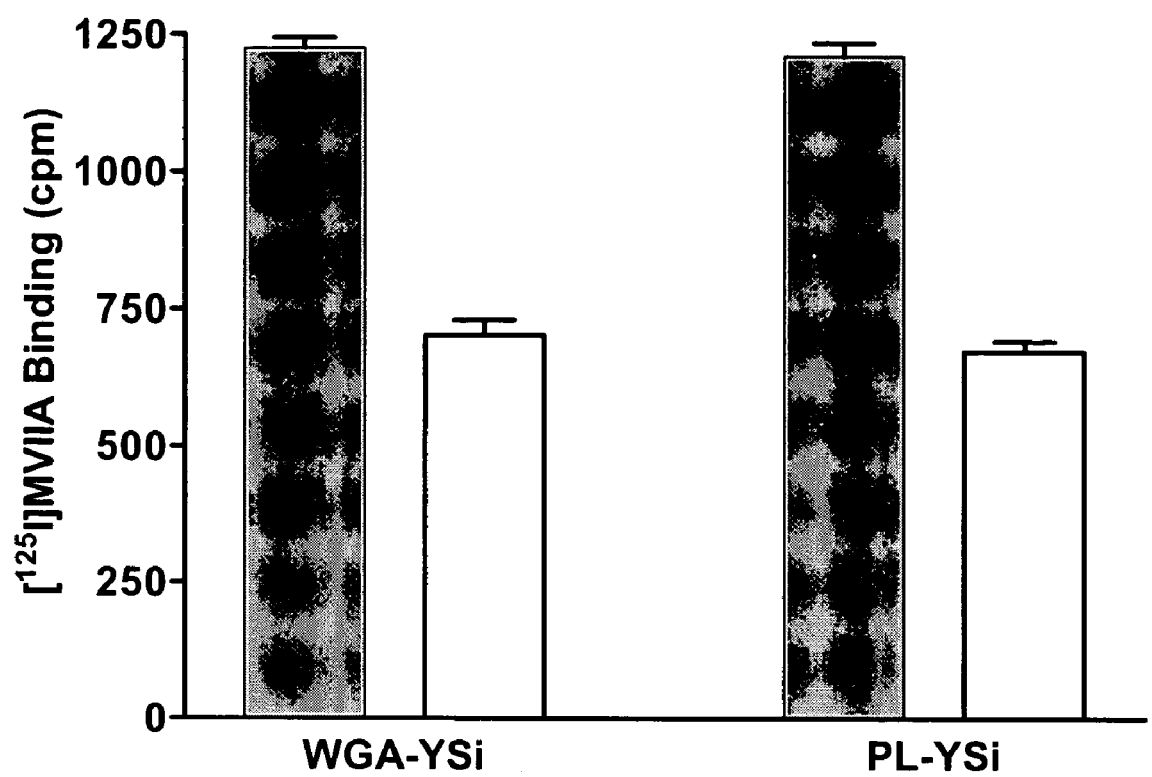
FIG. 10 is a graph illustrating the binding of [$^{125}$I]MVIIA to ion channels in cell membranes precoupled to yttrium silicate beads coated with wheat germ agglutinin (WGA-YSi) or polylysine (PL-Ysi). Total binding is represented as a gray bar, and nonspecific binding is represented as a white bar.

Light energy emitted from the microtiter plate was measured using a Packard Top Count™ scintillation counter. Results are shown in FIG. 10. Total binding is shown at bar A, while nonspecific binding is shown at bar B. [$^{125}$I]MVIIA is shown in cpm on the Y-axis. It was observed that non-specific binding was higher than assays utilizing PVT-WGA Beads.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

We claim:

1. An assay system for detecting molecules that modulate calcium ion channels that are known to interact with one or more specified ligands, the assay system comprising:
   a. isolated cell membranes or portions thereof comprising calcium ion channels;
   b. support bodies comprising scintillant and a coupling agent that associates with the isolated cell membranes or portions thereof; and
   c. a specified ligand that is selected to bind the calcium ion channel, the ligand comprising a scintillant-activating label,
   wherein association of the support bodies with the isolated cell membranes or portions thereof and binding of the specified ligand to the calcium ion channel results in emission from the scintillant of the support bodies, and wherein, in the presence of a test molecule that modulates the calcium ion channel, the emission from the scintillant of the support bodies changes.

2. The assay system according to claim 1 wherein the isolated cell membranes or portions thereof are obtained from cells expressing native calcium ion channels.

3. The assay system according to claim 1 wherein the isolated cell membranes or portions thereof are obtained from recombinant cells expressing the calcium ion channel from exogenous DNA.

4. The assay system according to claim 1 wherein the isolated cell membranes or portions thereof are artificial membranes.

5. The assay system according to claim 1 wherein the support bodies comprise beads.

6. The assay system according to claim 1 wherein the coupling agent associates with the isolated cell membranes or portions thereof in a non-specific manner.

7. The assay system according to claim 6 wherein the coupling agent relies upon the negative charge of the isolated cell membranes or portions thereof to associate with the isolated cell membrane or portions thereof.

8. The assay system according to claim 1 wherein the ligand is a peptide.

9. The assay system according to claim 1 wherein the scintillant-activating label is a radioactive isotope.

10. The assay system according to claim 1 wherein the molecule is selected from the group consisting of N-type and P/Q-type calcium ion channel modulators.

11. The assay system according to claim 1 wherein, in the presence of a test molecule that interacts with the calcium ion channels, the emission from the scintillant of the support bodies decreases.

* * * * *